(12) United States Patent
Krettek

(10) Patent No.: US 11,357,636 B2
(45) Date of Patent: Jun. 14, 2022

(54) MAGNETIC ARTIFICIAL JOINT

(71) Applicant: MEDIZINISCHE HOCHSCHULE HANNOVER, Hannover (DE)

(72) Inventor: Christian Krettek, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 1 day.

(21) Appl. No.: 16/967,453

(22) PCT Filed: Feb. 5, 2019

(86) PCT No.: PCT/EP2019/052762
§ 371 (c)(1),
(2) Date: Aug. 5, 2020

(87) PCT Pub. No.: WO2019/154800
PCT Pub. Date: Aug. 15, 2019

(65) Prior Publication Data
US 2021/0030554 A1 Feb. 4, 2021

(30) Foreign Application Priority Data
Feb. 8, 2018 (EP) .................................... 18155752

(51) Int. Cl.
| | |
|---|---|
| *A61F 2/30* | (2006.01) |
| *A61F 2/32* | (2006.01) |
| *A61F 2/40* | (2006.01) |

(52) U.S. Cl.
CPC .............. *A61F 2/4081* (2013.01); *A61F 2/32* (2013.01); *A61F 2/40* (2013.01); *A61F 2/4014* (2013.01);
(Continued)

(58) Field of Classification Search
CPC ...... A61F 2/30; A61F 2/32; A61F 2/40; A61F 2/42; A61F 2/4081; A61F 2/4014;
(Continued)

(56) References Cited

U.S. PATENT DOCUMENTS

| | | | |
|---|---|---|---|
| 4,024,588 A | 5/1977 | Janssen et al. | |
| 9,561,111 B1 * | 2/2017 | Goodman | A61F 2/4081 |

(Continued)

*Primary Examiner* — Dinah Baria
(74) *Attorney, Agent, or Firm* — WC&F IP

(57) ABSTRACT

The invention relates to a prosthesis for implantation into a living body in the form of a magnetic artificial joint, in particular an artificial shoulder joint, comprising: a) a first prosthesis member comprising a socket member, b) a second prosthesis member comprising a head member, c) one of the socket member and the head member is at least partially composed as a permanent magnet and the other one of the socket member and the head member is at least partially composed of a magnetic material, or the socket member and the head member are both at least partially composed as a permanent magnet, d) the socket member comprises a recess on a surface side to be coupled with the head member, the recess comprising a concavely contoured contact surface, e) the head member comprises a projection on a surface side to be coupled with the socket member, the projection comprising a convexly contoured contact surface, f) the convexly contoured contact surface is adapted to the concavely contoured contact surface, such that the head member can be coupled in a rotatably jointed manner to the socket member in the nature of a ball/ball-socket joint, g) wherein the convexly contoured contact surface can perform a generally slip-fee rolling motion or a combined slipping and rolling motion on the concavely contoured contact surface in reaction to a change of an angle between the first and the second prosthesis member, and the convexly contoured contact surface can be shifted across the concavely contoured contact surface within a shifting area.

11 Claims, 5 Drawing Sheets

Figure 1:
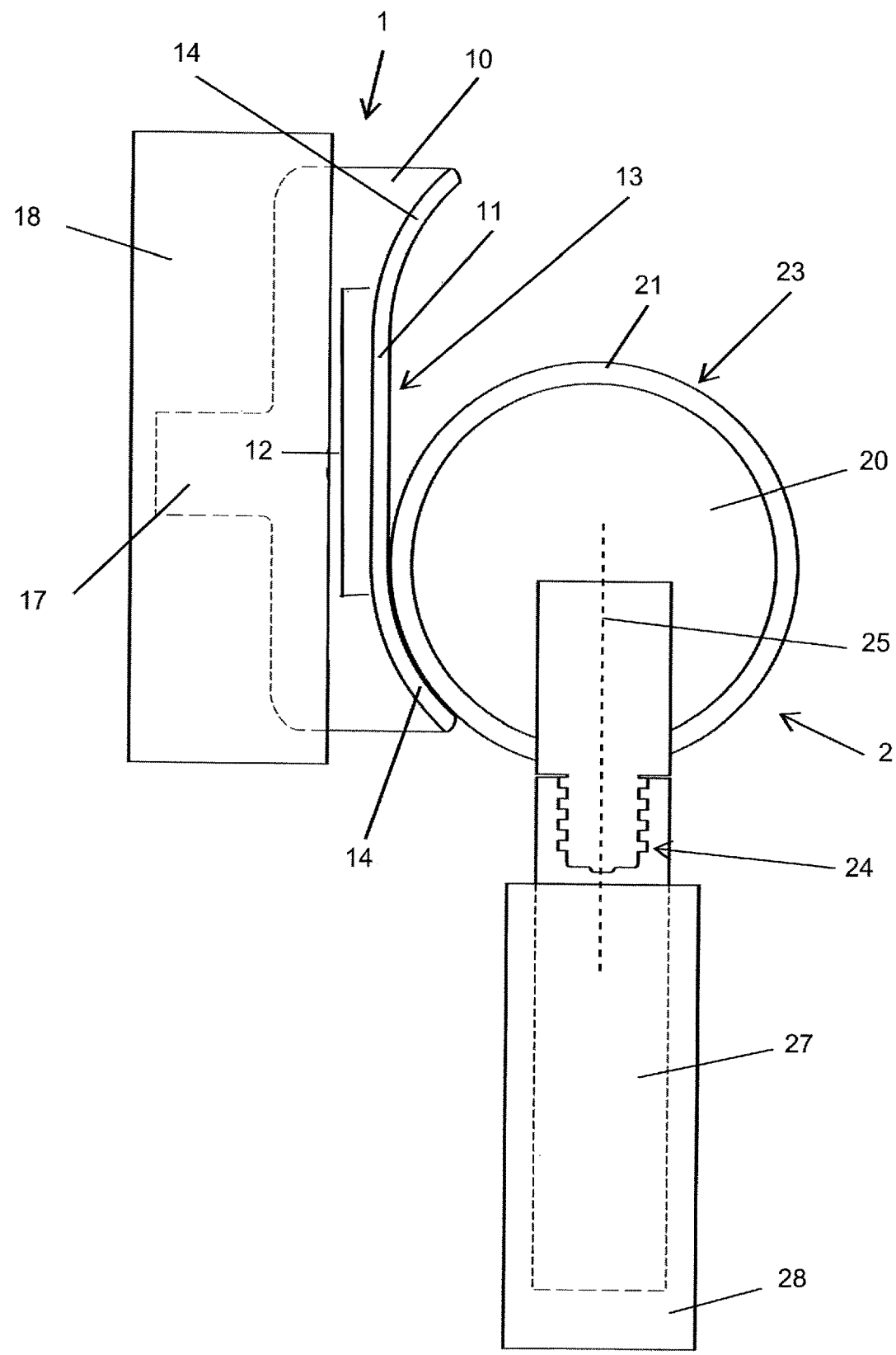

(52) U.S. Cl.
CPC ....... *A61F 2/30* (2013.01); *A61F 2002/30079* (2013.01); *A61F 2002/30242* (2013.01); *A61F 2002/30253* (2013.01); *A61F 2002/30364* (2013.01); *A61F 2002/30649* (2013.01); *A61F 2002/30934* (2013.01); *A61F 2002/4037* (2013.01)

(58) Field of Classification Search
CPC .... A61F 2002/2871; A61F 2002/30369; A61F 2002/30319; A61F 2002/30365; A61F 2002/30367; A61F 2002/30652; A61F 2002/30654; A61F 2002/30079; A61F 2002/30364; A61F 2002/30934; A61F 2002/30649; A61F 2002/4037; A61F 2002/30242; A61F 2002/30253
See application file for complete search history.

(56) References Cited

U.S. PATENT DOCUMENTS

| | | | |
|---|---|---|---|
| 2002/0087213 A1 | 7/2002 | Bertram | |
| 2010/0145464 A1 | 6/2010 | Sidhom | |
| 2010/0234959 A1* | 9/2010 | Roche | A61F 2/40 623/19.13 |
| 2012/0290093 A1* | 11/2012 | Hansell | A61F 2/442 623/17.16 |
| 2017/0224495 A1 | 8/2017 | Rogachefsky | |

\* cited by examiner

MAGNETIC ARTIFICIAL JOINT

The invention relates to a prosthesis for implantation into a living body in the form of a magnetic artificial joint, in particular an artificial shoulder joint. The artificial joint can be an articulated joint as a replacement for a shoulder joint, hip joint, knee joint or other joint of a living being.

In the case of a shoulder joint, due to certain diseases a defect and as a consequence a loss of functionality of the muscles and/or tendons can happen. In case of irreparable defects, it is known to implant an inverse or reverse shoulder prosthesis which provides for a certain functionality of the shoulder. However, the in-verse/reverse shoulder prosthesis requires an intact delta muscle. In case of a complete loss of functionality of the delta muscle, the holding and stabilizing function of this muscle is missing. As a result, the whole weight of the arm stresses the nerval plexus. In many cases this causes heavy pain.

A total shoulder replacement by magnetic arthroplasty has been proposed by Levon Doursounian et al, published in the Journal of Elbow Surgery, January/February 1998, pages 13 to 18.

It is an object of the present invention to present an improved prosthesis in the form of a magnetic artificial joint.

This object is achieved by a prosthesis for implantation into a living body in the form of a magnetic artificial joint, particularly in an artificial shoulder joint, comprising:
a) a first prosthesis member comprising a socket member,
b) a second prosthesis member comprising a head member,
c) one of the socket member and the head member is at least partially composed as a permanent magnet and the other one of the socket member and the head member is at least partially composed of a magnetic material, or the socket member and the head member are both at least partially composed as a permanent magnet,
d) the socket member comprises a recess on a surface side to be coupled with the head member, the recess comprising a concavely contoured contact surface,
e) the head member comprises a projection on a surface side to be coupled with the socket member, the projection comprising a convexly contoured contact surface,
f) the convexly contoured contact surface is adapted to the concavely contoured contact surface, such that the head member can be coupled in a rotatably jointed manner to the socket member in the nature of a ball/ball-socket joint,
g) wherein the convexly contoured contact surface can perform a generally slip-free rolling or a combined slipping and rolling motion on the concavely contoured contact surface in reaction to a change of an angle between the first and the second prosthesis member, and the convexly contoured contact surface can be shifted across the concavely contoured contact surface within a shifting area.

The invention provides for a stabilized and rotatable connection as a replacement for a natural joint of a living body. Therefore, at least a passive movability of the parts of the living body is maintained. The stability of the connection between the first and the second bone structure is improved. Further, the comfort for the user is enhanced and traction related pain can be significantly reduced. The part of the living body, e.g. the arm can be passively moved in certain definable functional positions, for example for supporting ingestion, personal hygiene or other activities in housekeeping or business.

An advantage of the invention is the improved functionality of a magnetic artificial joint combined with a very easy to use capability. Since the socket member and the head member always have a tendency to attract each other, the correct positioning of the head member relative to the socket member is automatically reestablished in case of any misalignment, e.g. caused by strong external forces.

In addition, the magnetic artificial joint of the invention allows for certain freedom and therefore some enhanced flexibility in the relationship between the head member and the socket member. This is achieved by shaping the concavely contoured contact surface in a way that some space is left for the convexly contoured contact surface, allowing the convexly contoured contact surface to perform the mentioned rolling motion and the shifting motion. Therefore, the convexly contoured contact surface is not adapted exactly to the concavely contoured contact surface over its whole area, but maybe in certain areas. This may be achieved by designing the concavely contoured contact surface with a minimum radius which is larger than the maximum radius of the convexly contoured contact surface. This provides the user with less resistance when performing an arm movement.

According to an advantageous embodiment the socket member comprises at least one outer holding member at the edge of the concavely contoured contact surface, wherein the rolling motion and/or the shifting motion of the head member is limited towards the edge of the concavely contoured contact surface by the at least one outer holding member. This provides for a limitation of the rolling and/or shifting motion with simple mechanical means. Further, such outer holding member provides for certain stop positions which support the user of the prosthesis in placing the arm at certain discrete positions. For example, the shifting area can be surrounded by one or more outer holding members. In one example, only one outer holding member in the form of a ring-shaped element is implemented. The ring-shaped element can also be fragmented into several outer holding members.

It is advantageous to design the concavely contoured contact surface in the area of the outer holding member with a larger inner radius than the outer radius of the convexly contoured contact surface. This provides for an easy low resistance rolling motion of the convexly contoured contact surface on the concavely contoured contact surface.

According to an advantageous embodiment the socket member comprises at least one inner holding member within the shifting area, in particular generally in the middle of the shifting area, wherein the rolling motion and/or the shifting motion of the head member within the shifting area is influenced and/or limited by the at least one inner holding member. This has the advantage that another stopping position for the second prosthesis member is provided within the shifting area. Such inner holding member can be easily found by the user due to its design in the form of a projection in the shifting area.

According to an advantageous embodiment the inner holding member is established in the form of a projection within the shifting area, which comprises a concavely contoured reception surface directed to the head member, wherein the convexly contoured contact surface of the head member can be received within the concavely contoured reception surface. In such way, the head member can be easily placed on the concavely contoured reception surface of the inner holding member. The concavely contoured reception surface acts as a seat for the head member. It is advantageous to design the concavely contoured reception surface with a radius which is larger than the radius of the convexly contoured contact surface. In addition, the concavely contoured reception surface may have an own shifting area where the convexly contoured contact surface can be shifted across the concavely contoured reception surface.

According to an advantageous embodiment the height of an inner holding member is less than the height of an outer holding member. This further supports the user in locating and using the inner holding member. For example, the height of the inner holding member may be 50% or less than the height of an outer holding member. The height can be measured as the perpendicular distance from the concavely contoured contact surface within the shifting area to the maximum protrusion of the inner holding member respective the outer holding member.

According to an advantageous embodiment the concavely contoured contact surface comprises an inner planar area. This provides for a certain freedom of movement of the head member relative to the socket member. The shifting area may extend throughout the whole inner planar area.

According to an advantageous embodiment the convexly contoured contact surface is generally globular or ellipsoidal shaped and/or comprises on its outer surface an additional spherical member which partially modifies the globular or ellipsoidal shaped contour of the convexly contoured contact surface. The generally globular or ellipsoidal shape provides for a large pivoting range between the first prosthesis member and the second prosthesis member. In case the additional spherical member is applied, the available space for the rolling motion and/or the shifting motion of the head member is further extended. Also, the pivoting range between the first prosthesis member and the second prosthesis member is extended.

According to an advantageous embodiment the additional spherical member is a separate part from the convexly contoured contact surface, which is fixated on the convexly contoured contact surface. This allows for a modular concept of the artificial joint. The additional spherical member can be fixated on the convexly contoured contact surface in case it is needed. The additional spherical member can be made at least partially for a permanent magnetic material or other magnetic material.

According to an advantageous embodiment, the prosthesis comprises:
a) the first prosthesis member comprises a first attachment element for attaching the first prosthesis member to a first bone structure of the living body, wherein the socket member is connected to the first attachment element,
b) the second prosthesis member comprises a second attachment element for attaching the second prosthesis member to a second bone structure of the living body, wherein the head member is connected to the second attachment element.

According to an advantageous embodiment the second prosthesis member comprises an axial joint, which couples the head member rotatably with the second attachment element, such that the head member can be rotated via the axial joint relative to the second attachment element at least in the longitudinal direction of the second prosthesis member. This provides an additional degree of freedom of movement within the artificial joint. By means of the axial joint, the user is able to perform axial movements of its arm. The axial joint defines a rotating axis, the second attachment element being rotatable around this rotating axis relative to the head member. In certain embodiments, the rotating axis may be a central rotating axis which intersects the center of the head member. In other embodiments, the rotating axis can be a decentral rotating axis, which does not intersect the center of the head member.

Figure 2:
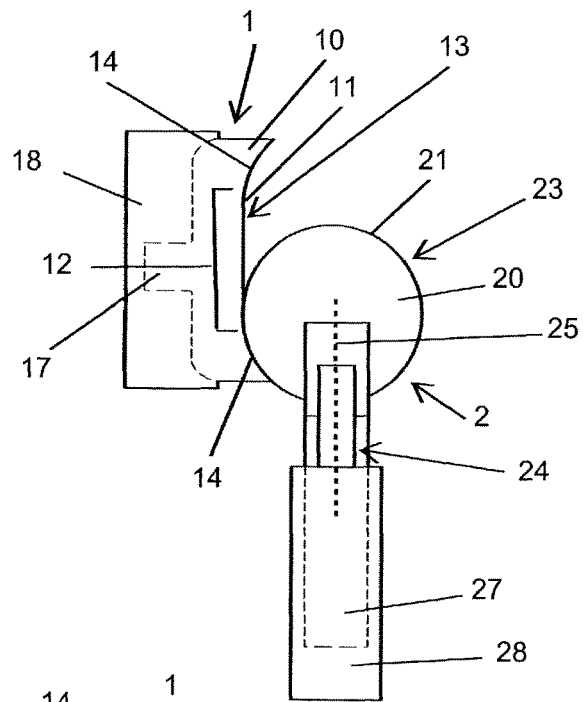
Figure 3:
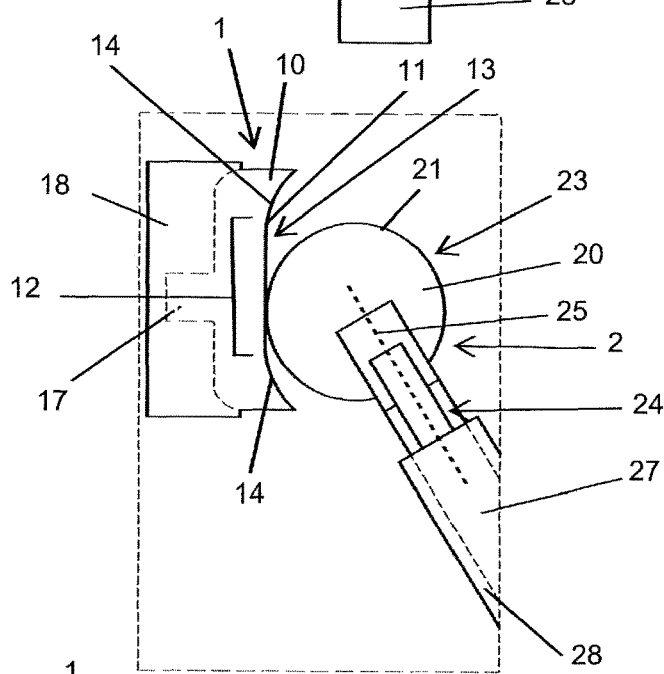
Figure 4:
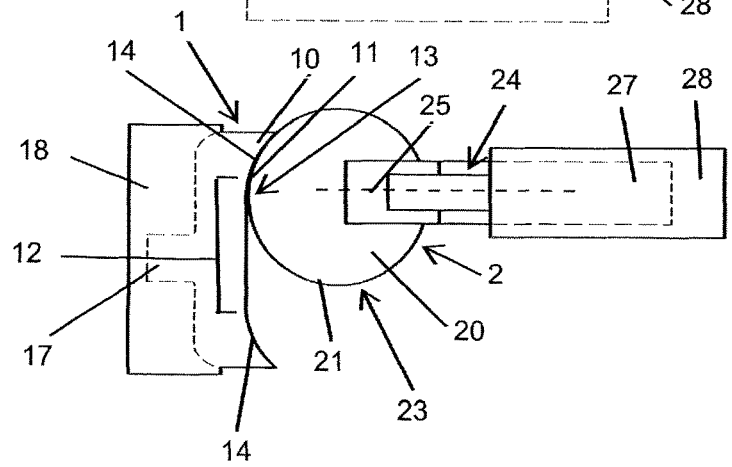
Figure 5:
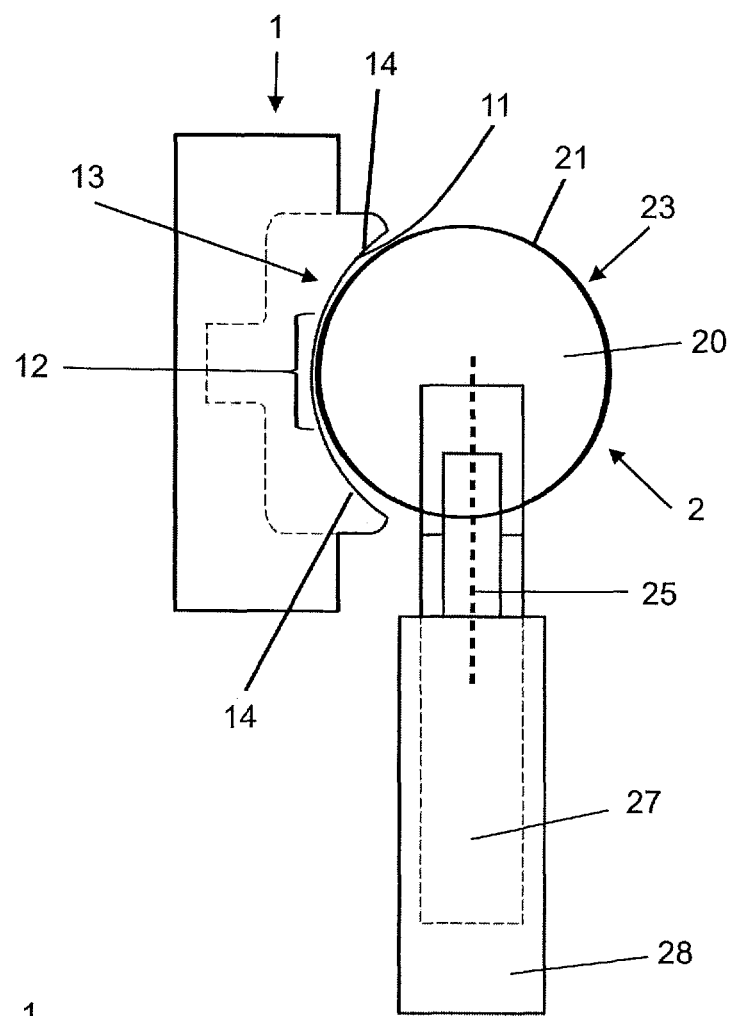
Figure 6:
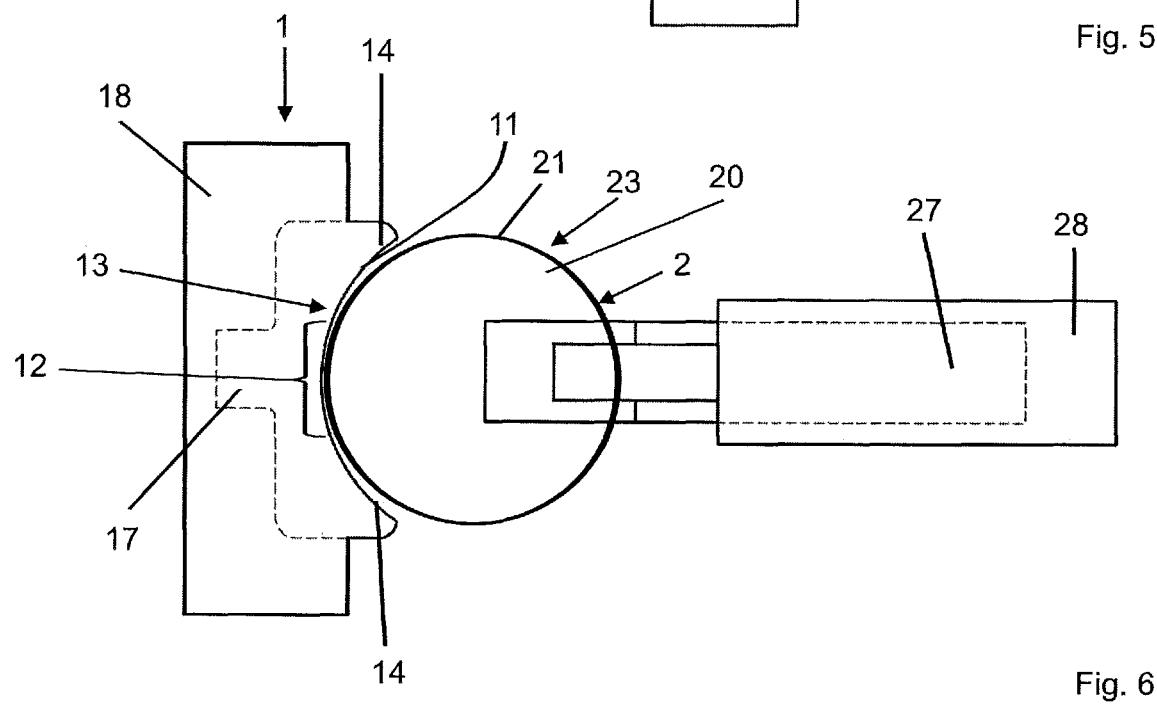
Figure 7:
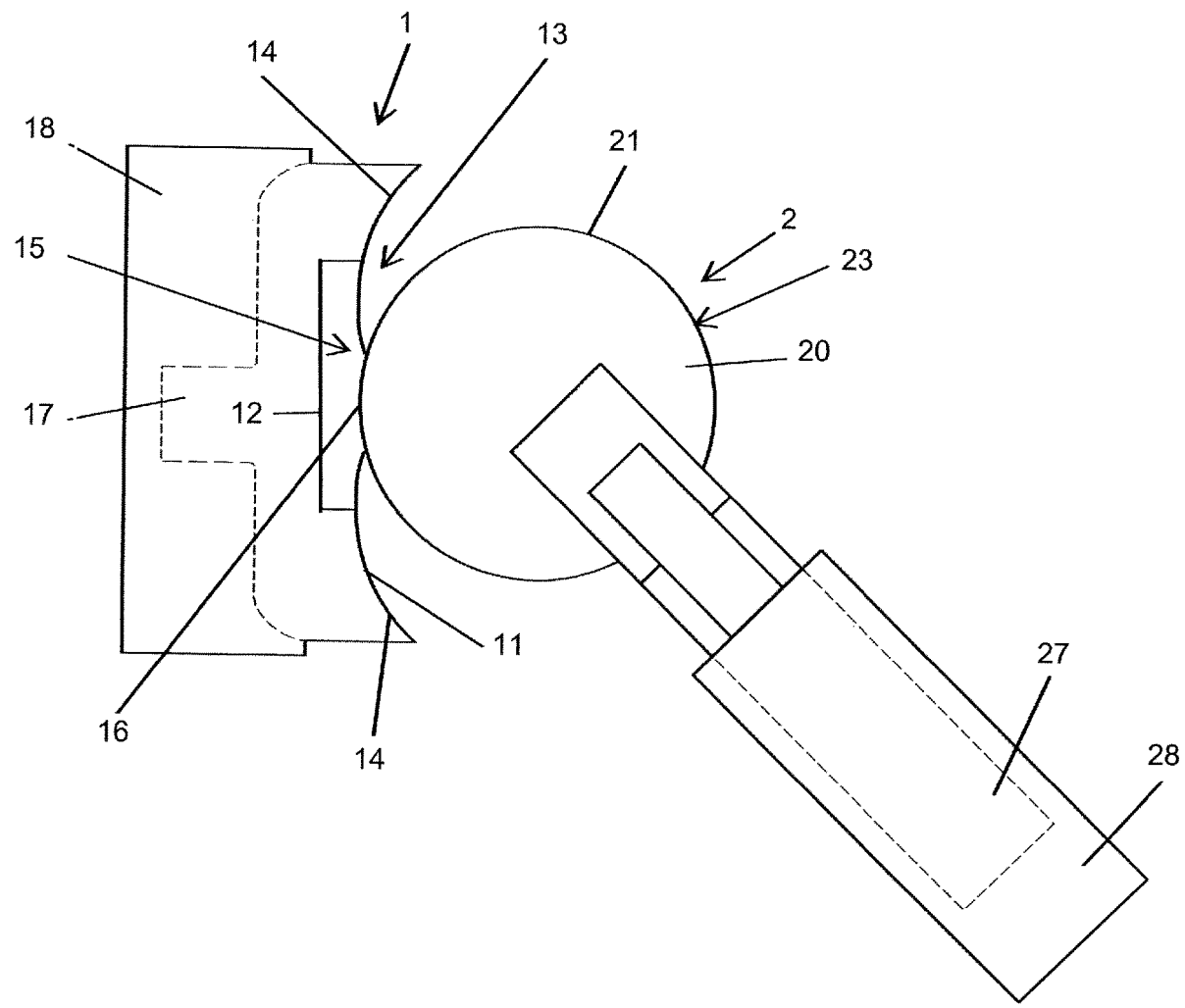
Figure 8:
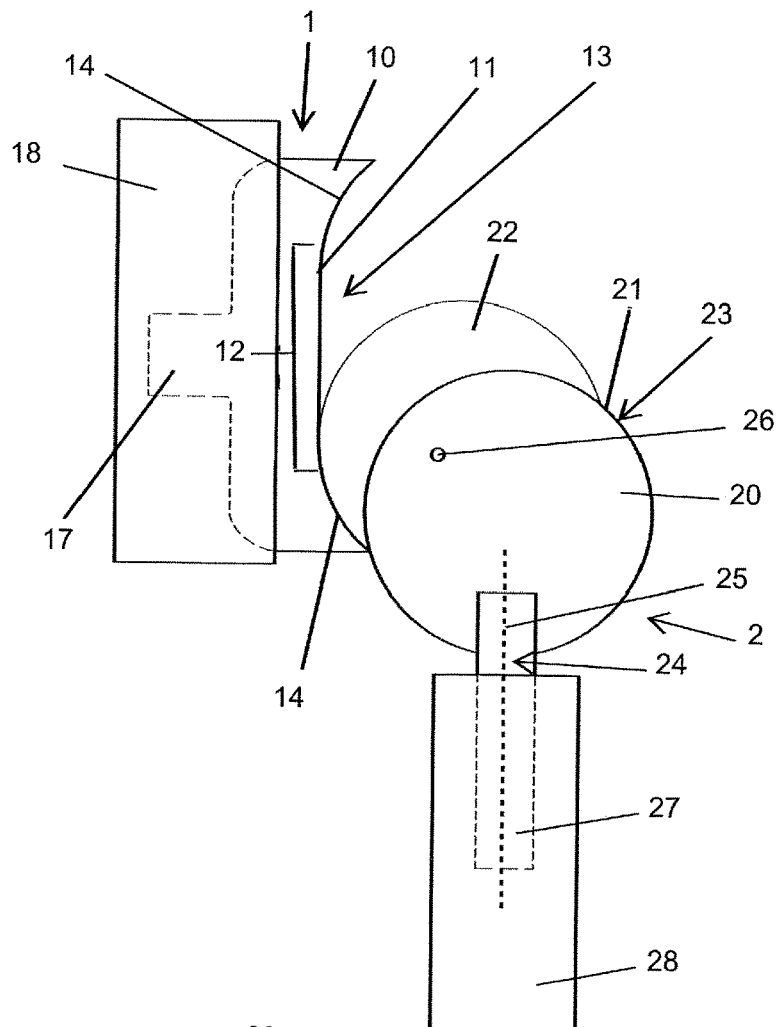
Figure 9:
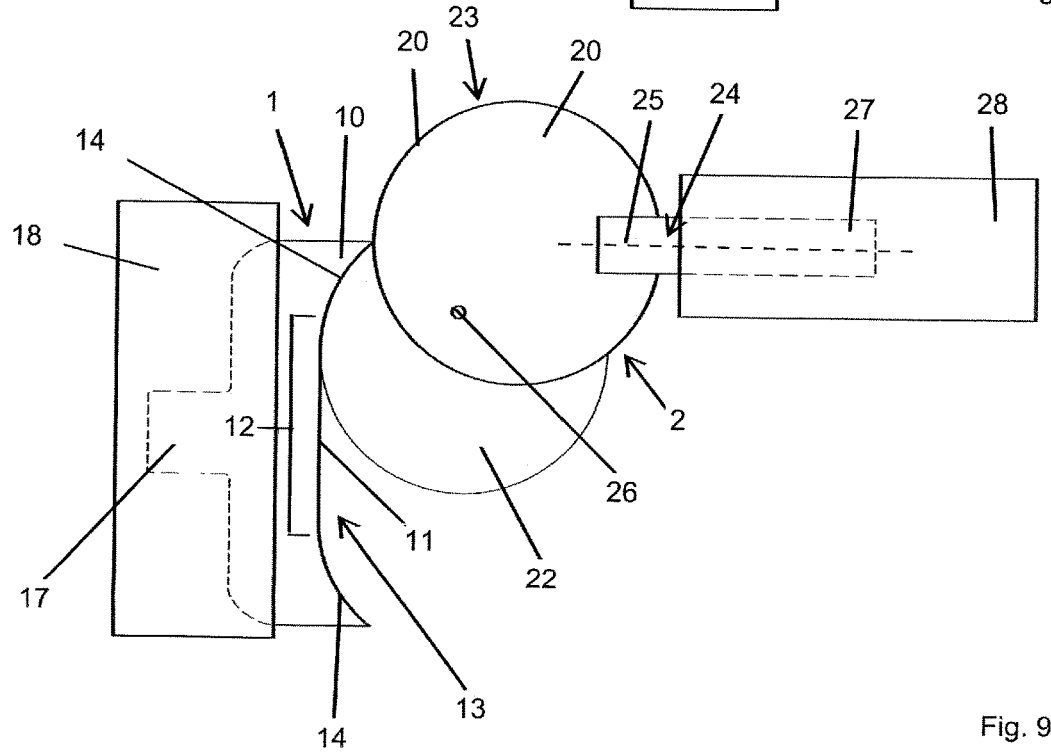

The invention is further described using the following figures.
FIG. 1—a first embodiment of an artificial joint;
FIGS. 2 to 4—the artificial joint of FIG. 1 in different angular positions;
FIGS. 5 to 6—a second embodiment of an artificial joint in different angular positions;
FIG. 7—a third embodiment of an artificial joint;
FIGS. 8 to 9—a fourth embodiment of an artificial joint in different angular positions.

The artificial joint is shown in the figures in a side view.
FIG. 1 shows a magnetic artificial joint comprising a first prosthesis member 1 and a second prosthesis member 2. The first prosthesis member 1 comprises a first attachment element 17 which serves as an interface for connecting or implanting the first prosthesis member 1 to a first bone structure 18 of the living body. The first bone structure 18 can be, in case of a shoulder joint, the scapula. The parts of the prosthesis member 1 which are in contact with the first bone structure 18, in particular the first attachment element 17, can be made of titanium or at least covered by titanium or other materials which allow osseous ingrowth.

The first prosthesis member 1 comprises a socket member 10 which serves as an interface to the second prosthesis member 2. The socket member 10 is connected to the first attachment element 17 by a rigid connecting structure of the first prosthesis member 1.

The socket member 10 comprises a recess 13 which can have any suitable hollow form. The recess 13 comprise a concavely contoured contact surface 11. The socket member 10 can be made from any magnetic material, for example of a steel which is used for implants. The concavely contoured contact surface 11 can have can be covered by a layer of a suitable material for reducing abrasive wear, e.g. by titanium nitrite or polyethylene. The coverage by titanium nitrite or polyethylene also provides for biocompatibility of the prosthesis.

The socket member 10 comprises one or more outer holding members 14 which are located at the edge of the concavely contoured contact surface 11. In the example shown in FIG. 1, the outer holding member 14 may be implemented in the form of a circular ring-shaped member which surrounds a shifting area 12 of the concavely contoured contact surface 11.

The second prosthesis member 2 comprises a second attachment element 27 which serves as an interface for attaching or implanting the second prosthesis member 2 to a second bone structure 28 of the living body, for example to the shaft of the humerus. The second attachment element 27 can be made of the same material as the first attachment element 17, e.g. from titanium.

The second prosthesis member 2 comprises a head member 20. In the shown example the head member 20 has a globular shape. However, the head member 20 shall have at least a projection 23 on a surface side to be coupled with the socket member 10. The projection 23 comprises a convexly contoured contact surface 21. The head member 20 can be partially or completely made of a permanent magnet material e.g. of magnetized ferritic steel, e.g. X2CrMoTi18-2 (material no. 1.4521).

The head member 20 is connected to the second attachment element 27 through a connection section of the second prosthesis member 2, e.g. by a rigid connection between the head member 20 and the second attachment element 27. In the example shown in FIG. 1, the connection between the head member 20 and the second attachment element 27 is not completely rigid but provides for the possibility of rotating the head member 20 relative to the attachment element 27 along a rotational axis 25. For this purpose, the connection section of the second prosthesis member 2 comprises an axial joint 24 which allows for such rotational motion. As an example, the axial joint 24 may be implemented in the form of a screwing connection where a female thread is connected to a male thread. The screwing connection is not completely locked, but allows for easy rotational movement.

For implementing an artificial joint, the head member 20 is located within the recess 13 of the socket member 10 such that the convexly contoured contact surface 21 is in contact with the concavely contoured contact surface 11. Since the recess 13 and therefore the concavely contoured contact surface 11 provides for more space as required for angular movement of the second prosthesis member 2, it is possible that the convexly contoured contact surface can perform a generally slip-free rolling or a combined slipping and rolling motion on the concavely contoured contact surface, when the angle between the first and second prosthesis member 1, 2 is changed. In addition, the convexly contoured contact surface can be shifted across the concavely contoured contact surface in a certain area, namely within the shifting area 12. The outer holding member 14 provides for a limitation of this motion of the head member 20. Because of its magnetic capabilities, the head member 20 and the socket member 10 are held together by magnetic forces.

The embodiment of the artificial joint shown in FIG. 1 allows for several movement capabilities of the second prosthesis member 2 relative to the first prosthesis member 1. For example, it is possible to perform a rolling motion of the head member 20 across the concavely contoured contact surface 11, wherein an additional holding force is generated at certain limitation points, when the head member 20 comes into contact with the outer holding member 14. As an example, FIG. 2 shows the second prosthesis member 2 in its lower end position. FIG. 3 shows the rolling motion of the head member 20 across the concavely contoured contact surface 11. FIG. 4 shows the limitation of the movement of the second prosthesis member 2 in an upper end position. This allows for stabilizing and holding the arm or other part of the living body in defined positions.

FIGS. 5 and 6 show an embodiment of the magnetic artificial joint, where the shifting area 12 is minimized to a very small area or maybe a single point. However, in this embodiment the inner radius of the concavely contoured contact surface 11 is larger than the outer radius of the convexly contoured contact surface 21. By this design there is still the possibility of rolling motion of the head member 20 over the convexly contoured contact surface with less frictional resistance compared to a sole shifting motion.

Another embodiment of an artificial joint is shown in FIG. 7. The embodiment comprises the features of the embodiment of FIG. 1. In addition, an inner holding member 15 is located within the shifting area 12. The inner holding member 15 allows for an enhanced holding and stabilizing force at a defined position within the shifting area 12. For example, when considering the movement shown in FIGS. 2 to 4, the inner holding member 15 allows for a stabilized position in a certain angular position of the second prosthesis member 2 relative to the first prosthesis member 1, for example at an angle of about 45 degrees. This gives possibility that the arm or other part of the living body can be stabilized and held in a certain additional functional position.

The embodiment shown in FIGS. 8 and 9 is based in the embodiment of FIG. 1. In addition, the head member 20 is equipped with an additional spherical member 22 which is mounted on the convexly contoured contact surface 21. This can help to enhance the movement area and movement angle between the first and second prosthesis member 1, 2 in an environment with limited space. The additional spherical member 22 can be arranged on the head member 20 for providing an eccentric pivot point 26 in combination with the bi-radial design of the head member 20.

The invention claimed is:

1. A prosthesis for implantation into a living body, comprising:
    a) a first prosthesis member comprising a socket member,
    b) a second prosthesis member comprising a head member,
    c) wherein one of the socket member and the head member is at least partially composed as a permanent magnet and the other one of the socket member and the head member is at least partially composed of a magnetic material, or
    the socket member and the head member are both at least partially composed as a permanent magnet,
    d) wherein the socket member comprises a recess on a surface side coupleable with the head member, the recess comprising a concavely contoured contact surface,
    e) wherein the head member comprises a projection on a surface side coupleable with the socket member, the projection comprising a convexly contoured contact surface,
    f) wherein the convexly contoured contact surface is adapted to the concavely contoured contact surface such that the head member is coupleable in a rotatably jointed manner to the socket member as a ball/ball-socket joint,
    g) wherein the convexly contoured contact surface is globular or ellipsoidal shaped and comprises on its outer surface an additional spherical member which modifies the globular or ellipsoidal shaped contour of the convexly contoured contact surface,
    h) wherein the convexly contoured contact surface comprising the additional spherical member is configured for performing a generally slip-fee rolling motion or a combined slipping and rolling motion on the concavely contoured contact surface in reaction to a change of an angle between the first and the second prosthesis member, and the convexly contoured contact surface can be shifted across the concavely contoured contact surface within a shifting area, wherein the additional spherical member is sized and positioned such that, at some angles between the first and the second prosthesis members, the additional spherical member contacts the concavely contoured contact surface while the convexly contoured contact surface does not contact the concavely contoured contact surface.

2. The prosthesis of claim 1, wherein the socket member comprises at least one outer holding member at an edge of the concavely contoured contact surface, wherein a rolling motion and/or a shifting motion of the head member is limited towards the edge of the concavely contoured contact surface by the at least one outer holding member.

3. The prosthesis of claim 1, wherein the concavely contoured contact surface has a larger radius than the convexly contoured contact surface.

4. The prosthesis of claim 1, wherein the socket member comprises at least one inner holding member within the shifting area, wherein a rolling motion and/or a shifting motion of the head member within the shifting area is influenced and/or limited by the at least one inner holding member.

5. The prosthesis of claim 4, wherein the at least one inner holding member is in a form of a projection within the shifting area which comprises a concavely contoured reception surface directed to the head member, and wherein the convexly contoured contact surface of the head member is receivable within the concavely contoured reception surface.

6. The prosthesis of claim 4, wherein a height of the at least one inner holding member is less than a height of an outer holding member.

7. The prosthesis of claim 4, wherein the least one inner holding member is generally within a central region of the shifting area.

8. The prosthesis of claim 1, wherein the concavely contoured contact surface comprises an inner planar area.

9. The prosthesis of claim 1, wherein the additional spherical member is a separate part from the convexly contoured contact surface, wherein the additional spherical member is fixated on the convexly contoured contact surface.

10. The prosthesis according to claim 1, further comprising:
 a) a first attachment element on the first prosthesis member for attaching the first prosthesis member to a first bone structure of the living body, wherein the socket member is connected to the first attachment element,
 b) a second attachment element on the second prosthesis member for attaching the second prosthesis member to a second bone structure of the living body, wherein the head member is connectable to the second attachment element.

11. The prosthesis according to claim 10, wherein the second prosthesis member comprises an axial joint which couples the head member rotatably with the second attachment element such that the head member is rotatable via the axial joint relative to the second attachment element at least in a longitudinal direction of the second prosthesis member.

* * * * *